United States Patent [19]

Beller

[11] Patent Number: 5,623,095
[45] Date of Patent: Apr. 22, 1997

[54] METHOD FOR CHEMICALLY ANALYZING A SOLUTION BY ACOUSTIC MEANS

[75] Inventor: Laurence S. Beller, Idaho Falls, Id.

[73] Assignee: The United States of America as represented by the Department of Energy, Washington, D.C.

[21] Appl. No.: 562,613

[22] Filed: Nov. 24, 1995

[51] Int. Cl.⁶ .................................................. G01N 29/02
[52] U.S. Cl. ........................................ 73/61.49; 73/61.79
[58] Field of Search .............................. 73/61.45, 61.49, 73/61.79, 64.53, 590, 596

[56] References Cited

U.S. PATENT DOCUMENTS

| | | | |
|---|---|---|---|
| 3,283,562 | 11/1966 | Heisig et al. | 73/590 X |
| 3,359,788 | 12/1967 | Colvin | 73/61.49 |
| 4,562,589 | 12/1985 | Warnaka et al. | 381/71 |
| 4,862,384 | 8/1989 | Bujard | 364/509 |
| 5,247,261 | 9/1993 | Gershenfeld | 324/716 |
| 5,306,644 | 4/1994 | Myerholtz et al. | 436/149 |
| 5,353,262 | 10/1994 | Yakymyshyn et al. | 367/149 |
| 5,357,484 | 10/1994 | Bates et al. | 364/727 |
| 5,473,934 | 12/1995 | Cobb | 73/61.49 |

FOREIGN PATENT DOCUMENTS

2942909  5/1981  Germany ............................ 73/61.49

*Primary Examiner*—Michael Brock
*Attorney, Agent, or Firm*—Thomas G. Anderson; Robert J. Fisher; William R. Moser

[57] ABSTRACT

A method and apparatus for determining a type of solution and the concentration of that solution by acoustic means. Generally stated, the method consists of: immersing a sound focusing transducer within a first liquid filled container; locating a separately contained specimen solution at a sound focal point within the first container; locating a sound probe adjacent to the specimen, generating a variable intensity sound signal from the transducer; measuring fundamental and multiple harmonic sound signal amplitudes; and then comparing a plot of a specimen sound response with a known solution sound response, thereby determining the solution type and concentration.

16 Claims, 6 Drawing Sheets

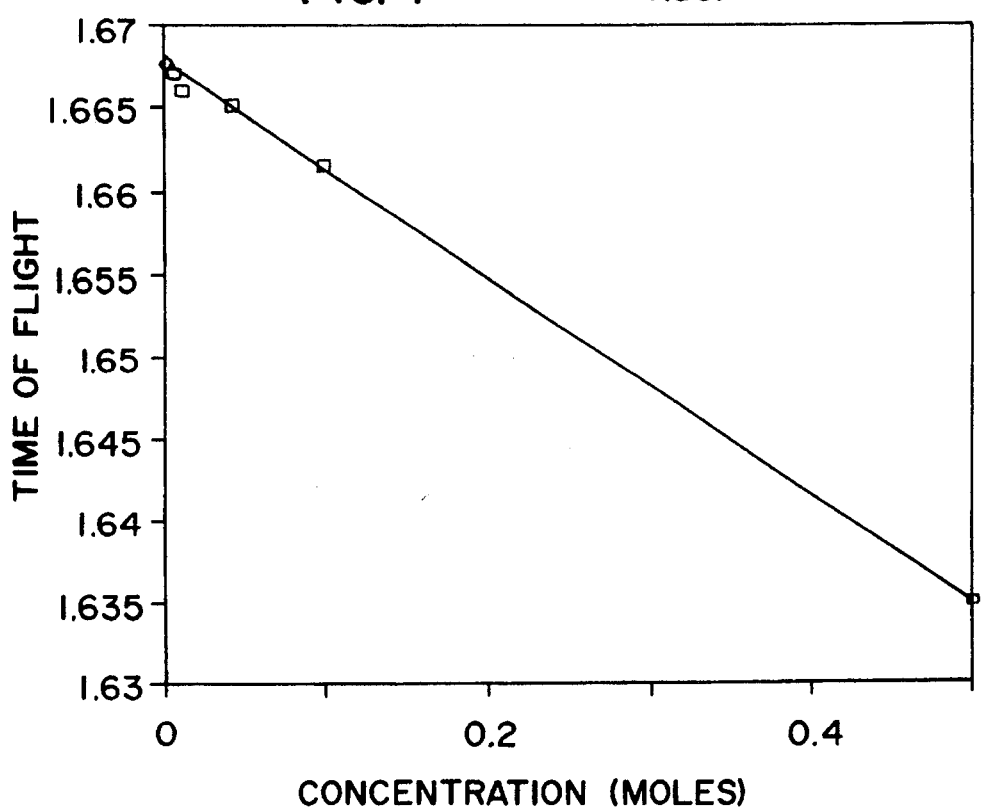
FIG. 1  NaCl
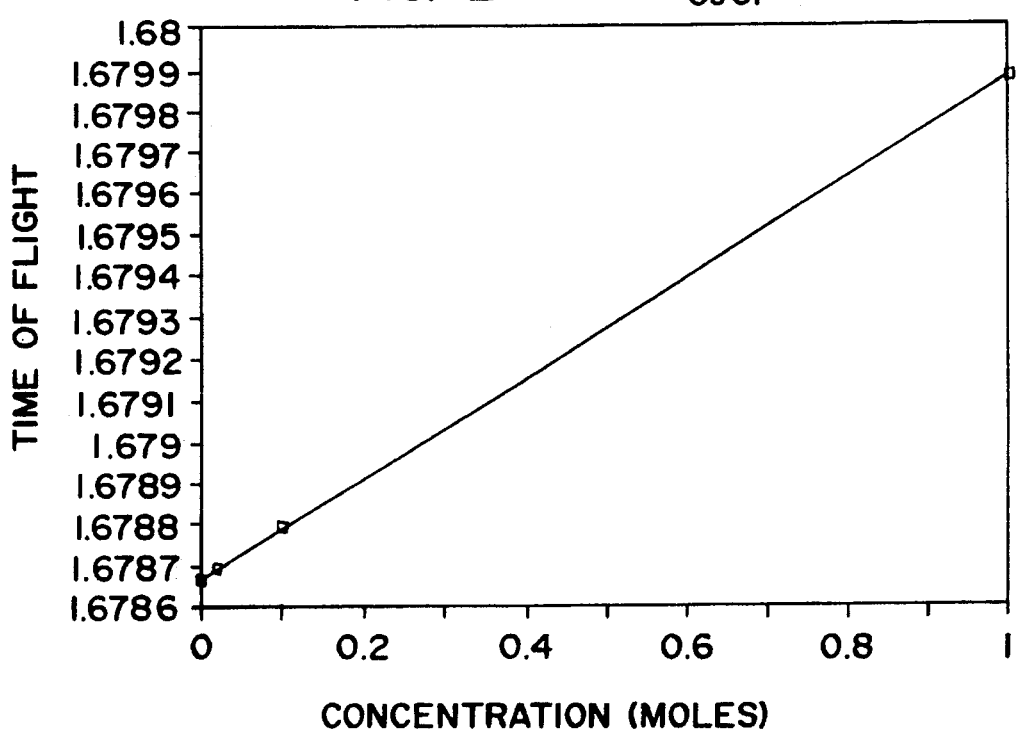
FIG. 2  CsCl

METHOD FOR CHEMICALLY ANALYZING A SOLUTION BY ACOUSTIC MEANS

CONTRACTUAL ORIGIN OF THE INVENTION

The United States Government has rights in this invention pursuant to Contract No. DE-AC07-94ID13223 between the United States Department of Energy and Lockheed Martin Idaho Technology.

TECHNICAL FIELD

This invention relates to a method of performing a qualitative and quantitative chemical analysis of an analyte within a closed container by external acoustic sensing means.

BACKGROUND OF THE INVENTION

The ability to measure solute concentration using aspects of nonlinear acoustic propagation, given a knowledge of which solvent and solute is present, and in some cases to distinguish qualitatively among known solvent/solute systems, has already been established in the relevant literature. However, the ability to do both qualitative and quantitative measurements simultaneously and to include more than one solvent/solute system in the analysis by these techniques does not currently exist.

Propagation of sound in solvents and their solutions has long been known to be nonlinear. The nonlinearity is manifested in the generation of harmonics and in velocity-dependent dispersion. The degree of nonlinearity is a function of the intensity of the sound wave. The degree of nonlinearity is also a function of the specific, detailed interactions among solvent and solute molecules, and under some conditions can be used to identify solvents and solutes. The degree of nonlinearity is conventionally expressed as the value of the parameter B/A, where A and B are the constants in the first two terms in a perturbative power-series expansion for the nonlinear strength.

Considerable current research has been directed toward medical applications of this phenomenon as a diagnostic tool. As a simple example, diseased organs often have a different water (and solute) content from healthy organs. More sophisticated applications-oriented research addresses identification of specific organic compounds. Spatial imaging of the sources of nonlinearity has also been done and these images reveal bone, blood vessels, and muscle distinctly because of differences in nonlinearity. Nearly all of the current work in the field is being done at "physiological" sound intensities. These intensities are characteristic of conventional medical ultrasound imaging, and are sufficiently low as to preclude injury to tissues.

Since the degree of nonlinearity is itself a function of acoustic intensity, it is to be expected on general principles that higher acoustic intensities will increase the resolution of small differences among solvent/solute systems, and that higher intensities may reveal additional aspects of the nonlinear interactions between solvent and solute.

The limiting sound intensities are dictated by solution cavitation, where the solute and solvent molecules are effectively torn apart. This phenomenon is used routinely, for example, in ultrasonic cleaners, and in certain techniques to modify equilibria in chemical reactions.

Applications of nonlinear phenomena as a measurement tool are different in principle from the current generation of acoustic chemical-sensing instrumentation which uses the speed of sound and related parameters to do chemical analysis for assessment of chemical agents in artillery shells and for arms control verification purposes. Measurement of the speed of sound with sufficient accuracy to quantify the small differences between solvent/solute systems requires knowledge of a precisely-known flight path. Manufacturing tolerances among similar containers are usually found to be large enough to introduce significant ambiguity into the measurement.

Current nonlinear-propagation and speed-of-sound methods produce ambiguous results with completely unknown solutions primarily because they yield only one parameter, the nonlinear strength parameter previously mentioned, B/A, or the speed of sound, neither of which are unique to the solution. Almost any solution can be simulated to give the same speed of sound or B/A by the properties of various mixtures of different solutions.

A series of experiments have been previously performed by the present inventor to provide background information relating to measurements of changes in the speed of sound in dilute solutions as a function of the molar concentration.

The experimental apparatus used consisted of a container, a piezoelectric transducer and solution specimen in bottles. A sharp pulse of ultrasonic energy at 5 MHZ is generated by the piezoelectric transducer within the container. The container also contains three annular target rings at fixed distances from the transducer to provide pulse/echo targets which define transit time. The time-of-flight is measured by digital means as the interval between the echoes from the target rings.

The full waveform is recorded by an analog-to-digital converter. The time interval between target-ring echoes is measured with a digital phase-matching technique that has a resolution approaching 100 picoseconds.

Solutions for experiments were prepared in half-decade steps in concentration from $5 \times 10^{-4}$ Molar (M) to 1.0M for NaCl, NaI, CsCl, and CsI, in two series. One series started at 1.0M, and the other at 0.5M.

The largest competing effect is that of temperature, which also changes the speed of sound in the solution. The temperature of the solutions was maintained constant at about 31° C.

The time of flight as measured was an accurately linear function of concentration over almost the full range measured in all solutes as seen in FIGS. 1 and 2. These are linear plots covering more than four decades in concentration of NaCl and CsCl respectively. The time scale on the ordinate is the transit time in this particular apparatus. The zero-concentration intercept is the transit time for water.

The slope of the transit-time vs. concentration is the calibration for the solute in each case, in units of μs/M for this apparatus. The slope and intercept were computed by the method of least-squares, weighted according to the experimental uncertainty at each point. Results are given in Table 1 and are plotted in FIGS. 1 and 2 for NaCl and CsCl, respectively.

TABLE 1

| Measured Calibration Slopes | |
|---|---|
| Solute | Slope (μs/M) |
| NaCl | −6.7524 |
| CsCl | 0.1219 |
| NaI | 2.6577 |
| CsI | 25.6011 |

The calibration for NaCl has a negative slope; the speed of sound increases as the concentration gets larger, at least up to 0.5M. The other solutes have increasingly positive calibrations. The slope for CsCl is small, but positive and easily measured with precision, as can be seen in FIG. 2.

The calibrations are shown in FIG. 3, relative to the time-of-flight for demineralized water, so that they apply to any container length.

The speed of sound in any medium is a function of the average intermolecular forces in that medium and of the mass of the individual particles involved. Solutes in a liquid change the intermolecular forces, which determine the sound speed. This work shows that, for very dilute solutions at least, the changes in intermolecular forces for a given low concentration solute are proportional to solute concentration in all cases investigated.

In a polar liquid, it can be expected that molecular or ion size, charge, hydration spheres, and similar variables also affect the intermolecular forces which control the speed of sound. Introductory texts generally state that the speed of sound is inversely proportional to the square root of the density, which is true in most cases. It is clearly not true here, however, since the density of the solution, proportional to the molecular weight in these measurements, clearly is not dominant, otherwise the calibration for NaCl could not be negative.

Consequently, the calibrations of FIG. 3 can be used directly and on-line for precise quantitative analysis of solutions of a single known solute and the difference in calibration slopes of FIG. 3 indicates that the technique can be also used for qualitative analysis as well.

Experiments in the field of solutions suggest that the nonlinearity mechanism involves hydration. Molecules in water solution can be described as being surrounded by hydration spheres of water molecules in "layers" or shells, the inner layer being most tightly bound, and other layers successively less well bound. The number and binding energy of water molecules in each layer is a function of solute molecule size, binding mechanism (e.g., electrostatic, Van Der Walls, etc.) and other parameters. The configuration and binding energies of the hydration sphere are unique properties of each solute molecule in each of its solvents, for many practical purposes at least. Liquids in general and pure solvent molecules in particular can be described as having the same structure, with each molecule being surrounded by an ordered array of other solvent molecules, the array becoming more disordered with distance, whether or not there are any solutes. Fully equivalent types of interactions affect other solvent systems, including, specifically, organic solvents.

To develop this theory of hydration and to explain the origin of nonlinear propagation, consider that an intense sound wave is propagating in a solution. During each compressive half-cycle of the sound wave, the solute, or solvent, molecule and all of its potential hydration sphere will be packed tightly together; the sound wave will be moving relatively heavy entities consisting of the solvent molecule and its hydration sphere, as it propagates. During each tensile half-cycle of the sound wave the tensile forces will strip off all or part of one or more hydration layers, depending on sound intensity, configuration, and binding energy of hydration layers. The sound wave will be moving relatively lighter entities during this part of the cycle.

Any harmonic motion in which the moving mass changes each half-cycle will generate harmonics, which is to say, is nonlinear. It is hypothesized that this is the mechanism for nonlinearity generation in solvents and their solutions.

One of the consequences of this hypothesis is that one expects the rate of nonlinearity generation with increasing intensity to change as the acoustic intensity becomes sufficient to strip all or part of each layer from the hydration sphere. Eventually the nonlinearity should stop increasing when there are no more layers to strip off, and this should happen at intensities lower than cavitation. At intermediate energies, any process which systematically changes the degree of hydration, such as complete removal of a hydration layer, will lower the rate of increase of nonlinearity with increasing acoustic intensity. Both complete and partial removal of the hydration sphere are termed "saturation" as described later.

SUMMARY OF THE INVENTION

A novel aspect of this inventive method is the introduction of variable acoustic intensity at significantly higher intensity compared to current practice. Under these conditions, previously unreported solvent/solute interactions come into play. The interactions are specific to each solvent/solute combination. Given these interactions, sufficient information will be available for both qualitative and quantitative analysis of unknown solutions, and potentially for solutions containing more than one solute and/or solvent.

The invention describes the use of acoustic (ultrasonic) intensity as an independent variable in the analysis of the composition of solutions by measurement of the strength of resulting nonlinearities, and shows that, at least under the conditions of the measurements, one can derive both identity of the solvent/solute combination and concentration, a feat that is not possible by present technology.

The method makes use of the whole range of intensities between "zero" and cavitation, a range not now being used in the art. The measurements suggest that each solution goes through "saturation" peaks and valleys one or more times in this intensity range; that the location, in terms of intensity, of these peaks and valleys is unique to the solvent/solute combination; and that these curves are probably additive. Therefore, the method should be able to distinguish identity and concentration of more than one solvent/solute combination simultaneously. The method still gives enough information to identify a single solution and its concentration. This method has a number of potential applications, i.e., radioactive cleanup, emergency service, process control, effluent monitoring, and identifying the spatial location of solutes in biological slides for acoustic microscopes.

Generally stated, the method consists of: immersing a sound focusing transducer within a liquid filled first container; locating a separately contained specimen solution at a sound focal point within the first container; locating a sound probe adjacent to the specimen, generating a variable intensity sound signal from the transducer; measuring a fundamental and multiple harmonic sound signal amplitudes; and then comparing a plot of a specimen sound response with a known solution sound response, thereby determining the solution type and concentration.

Other objects, advantages, and capabilities of the present invention will become more apparent as the description proceeds.

BRIEF DESCRIPTION OF THE DRAWINGS

FIG. 1 is a graph of time-of-flight (transit time) vs. molar concentration (M) for a sodium chloride (NaCl) solution.

FIG. 2 is a graph of time of flight vs. molar concentration for a cesium chloride solution.

DETAILED DESCRIPTION OF THE INVENTION

Figure 4:
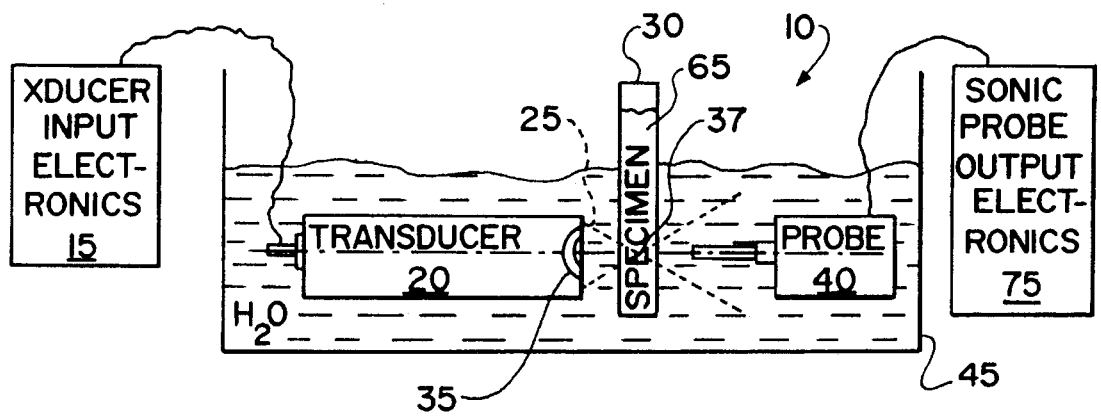
FIG. 4 is a schematic diagram of the acoustic apparatus used in experiments which support the present inventive method.

Referring to FIG. 4, the experimental apparatus used for this method of solution quantitative and qualitative analysis is generally illustrated at 10.

The input electronics 15 generates the variable intensity drive voltage to activate the submerged, beaming acoustic transducer 20. The acoustic beam 25 is focused on the sealed specimen culture tube or container 30 at a distance of about 25 mm, by a 25 mm diameter, 1.0 MHZ, curved piezoelectric crystal 35. Container 30 holds specimen 65.

The focal spot 37, between two and three wavelengths in diameter, located at the center of the culture tube container 30, contained most of the sound produced by the large-diameter transducer 35. The intensities produced are insufficient to cavitate water, but can be increased significantly by a number of means.

A 1-mm diameter ultrasonic field probe 40 having a flat response up to about 15 MHZ was placed in the far field, beyond focus, to detect the modified sound wave for analysis.

The acoustic apparatus was placed in a large water bath container 45 during measurements. The water bath provided for sound propagation between the transducer 20, culture tube 30, and probe 40, and provides cooling for the transducer. The bath container 45 size and geometry minimized effects of reflected sound.

Figure 5:
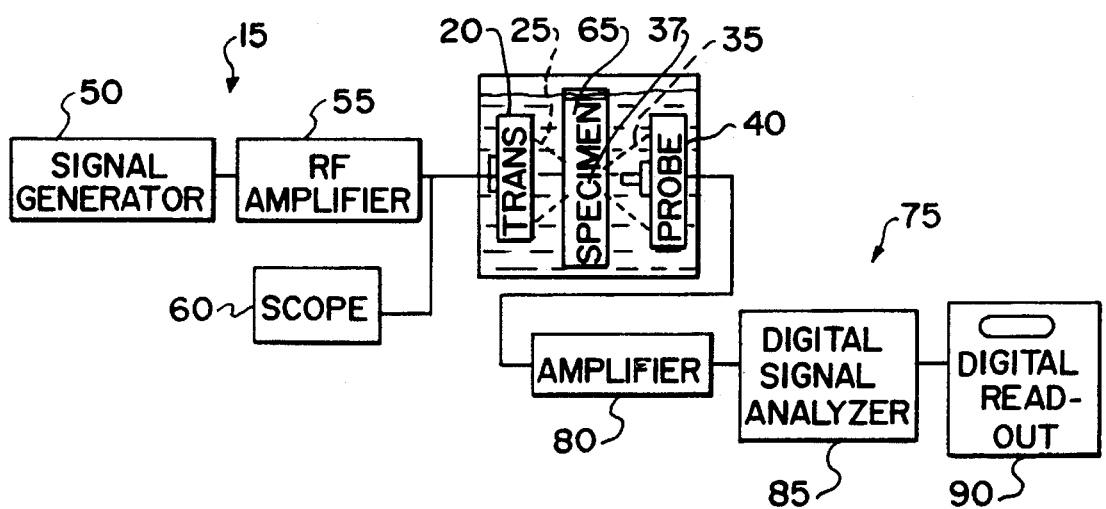
FIG. 5 is an electrical block diagram of the apparatus used in developing the present method.

The electronics instrumentation for the chemical analysis measurements is shown schematically in FIG. 5. A signal generator 50 is used to provide a low-level continuous sine-wave signal to the broadband linear amplifier 55 that controls input to the transducer 20. The amplifier 55 output voltage can be monitored by oscilloscope 60. After the acoustic beam 25 passes through focal spot 37 in specimen 65, the modified signal 70 containing harmonics is picked up by probe 40 and directed to output electronics 75. The output electronics 75 includes output amplifier 80 which amplifies and directs the acoustic signal to a digital signal analyzer 85 and digital readout 90. The digital signal analyzer (DSA) 85 provides high-resolution digital samples at a 1-GHz rate, and is used to perform signal averaging and fast Fourier transforms on the selected waveforms. Amplitudes of the fundamental and first three harmonics are measured using a DSA cursor system and digital readout 90. The digital readout 90 could also be replaced by a computer that would store the data, plot the data and compare the response spectrum to known solutions and concentrations to determine a match of test specimen to known specimen. Amplitudes of the harmonics are read as decibels (dB) below that of the fundamental in each case.

The noise level of the system is determined by the harmonic content of the signal generator 50, and is a function of frequency. The noise level is typically −50 dB, −55 dB, and −60 dB at the frequencies of the first three harmonics respectively. Maximum amplitude of the fundamental signal is of the order of 1 dB.

Although this invention is described as using a transducer and a separate field probe receiver, it is also possible to make measurements in pulse/echo geometry where there is only one transducer; i.e., fire a short pulse, then listen with the same transducer for the echo off the back wall of a container and analyze the echo. It is also possible to omit the water bath container and place the transducer and receiver against a solution container wall to monitor the unknown solution within that container or pipe containing the solution.

EXPERIMENTS

The experiments were designed to measure a number of solutions to develop a qualitative and quantitative analysis. The experiments were intended to provide primarily qualitative results on types of phenomena and their magnitudes.

Figure 3:
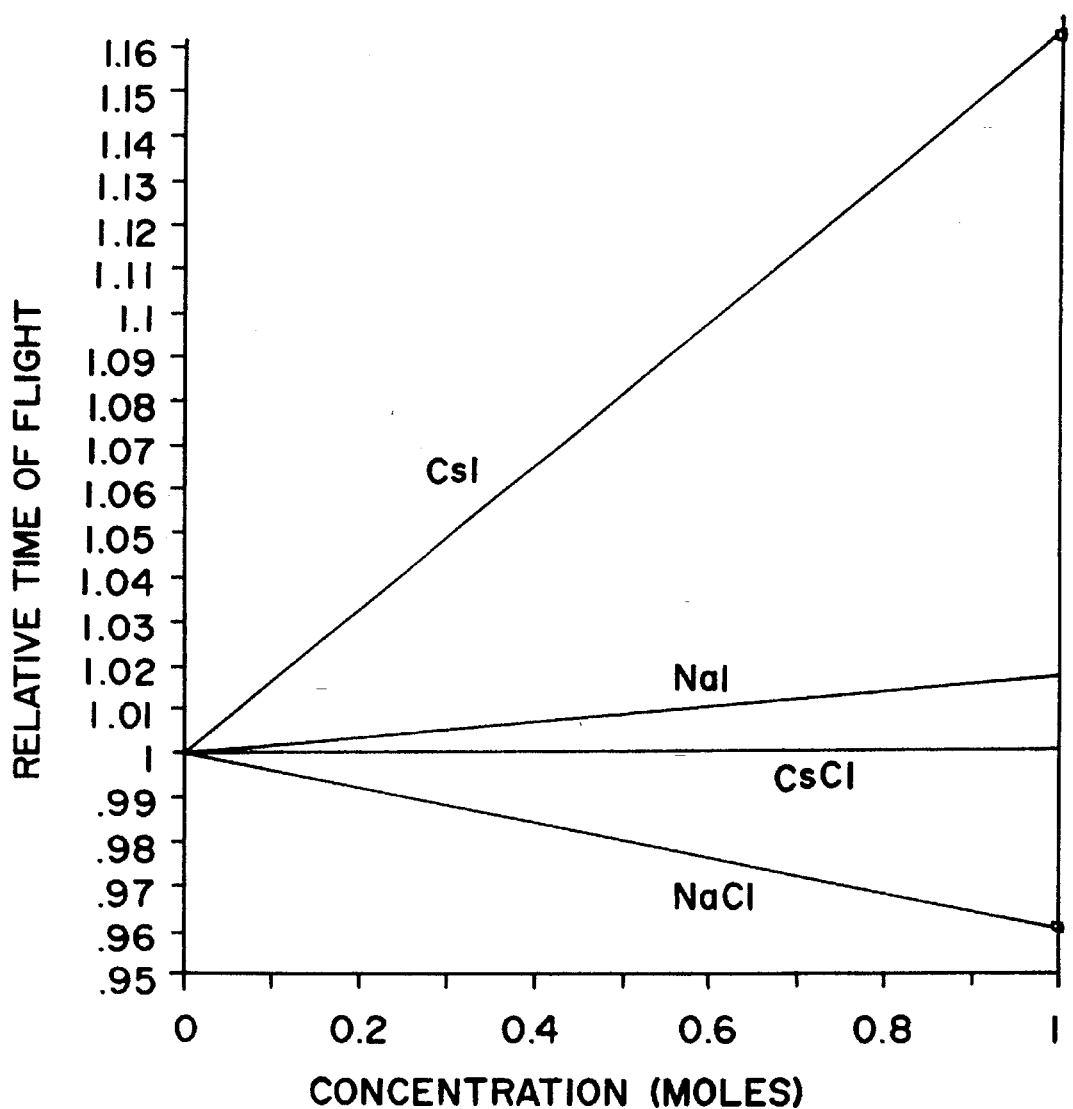
FIG. 3 is a graph of time-of-flight relative to water vs. molar concentration for four solutions.

The experimental test solutions are given in Table 2. The two ionic salts, NaCl and CsI, were chosen because the previously described experimental work showed them to be highly nonlinear, but with opposite signs for velocity dispersion as shown in FIGS. 1–3 and described in the "Background". The organics provide an increasingly "hydrated" series for which data at physiological intensities are available in the literature.

TABLE 2

| Experimental Materials | | |
|---|---|---|
| Solvent | Solute | Concentrations |
| Water | None | 100% |
| Water | NaCl | 0.5, 0.1, and 0.05 Molar |
| Water | CsI | 0.5, 0.1, and 0.05 M |
| Methyl Alcohol | None | 100% |
| Benzyl Alcohol | None | 100% |
| Ethylene Glycol | None | 100% |

The solutions were contained in sealed individual 19-mm diameter polyethylene biological culture tubes 30 since polyethylene provides a better acoustic-impedance match to water than does glass, and thus delivers more intensity in the measurement volume. Each solution 65 was measured three times over a transducer input range of 3 to 80 volts. Each day's measurement included a culture tube of water for standardization.

The most general results are quantitative and depend on the shape of the curves of amplitude of the fundamental frequency and harmonics as a function of drive voltage to the sending transducer 20. Drive voltage is measured and used as a proxy for the independent variable for acoustic intensity.

The most information on nonlinear propagation was found to reside in the fundamental and first harmonic in each case, but there is some additional information in the second and third harmonics.

Figure 6:
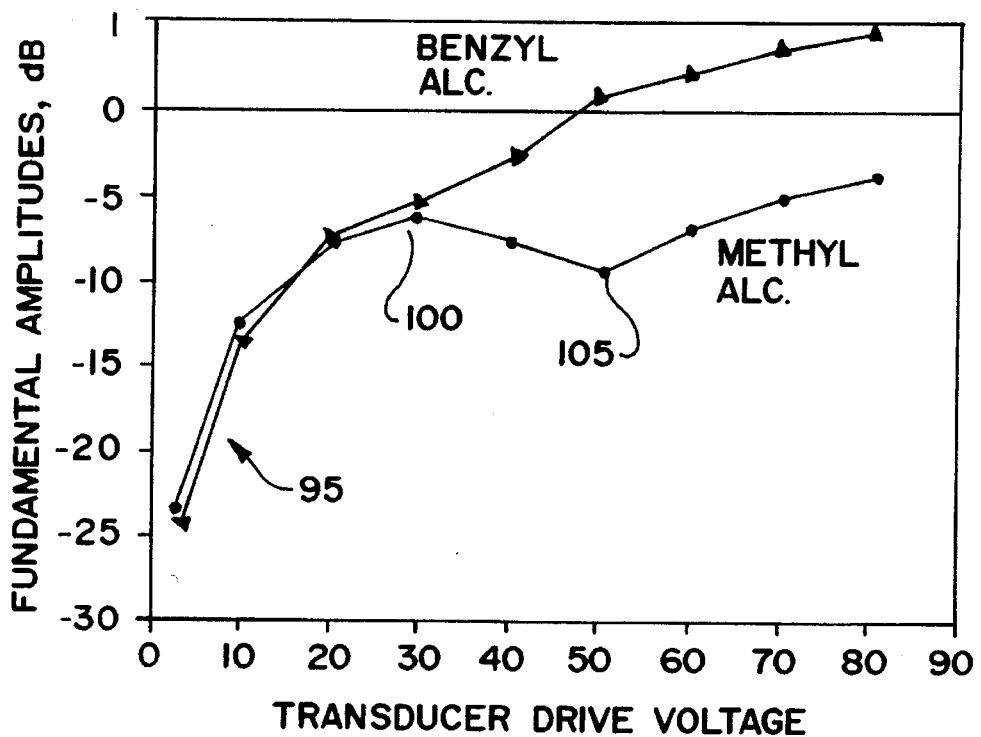
FIG. 6 is a graph of fundamental acoustic amplitude vs. transducer drive voltage for benzyl and methyl alcohols.

In FIG. 6, it is noted that for both benzyl and methyl alcohols, the fundamental rises linearly in proportion to drive voltage between 3 and 30 volts as at 95. It should be noted that in FIGS. 6–9 what is described as linear appears as a curve or exponential rise and what is described as exponential appears as a straight line. This is because the amplitudes are given in decibels (dB) which are exponential values, making these graphs semilog graphs. There are two inflection points 100 and 105 in the methyl alcohol amplitude shown in FIG. 6, which are discussed separately below. Linear proportionality indicates only that dissipative attenuation is not a significant factor at the power levels considered.

Figure 7:
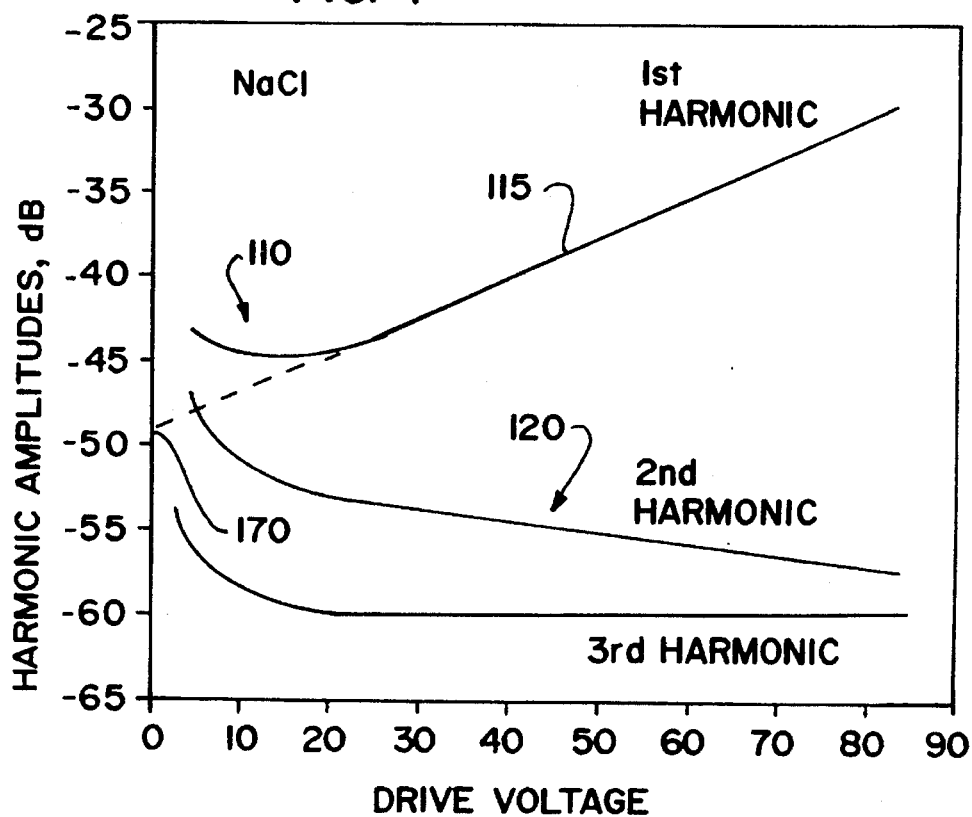
FIG. 7 is a graph of harmonic amplitudes vs. drive voltage for sodium chloride (NaCl).

Referring now to FIG. 7, most of the energy in the harmonics is confined to the first harmonic as at 115. The amplitudes of all three harmonics generally decline in the excitation region between 3 V and 10 V as at 110. Above 10 V excitation, the first harmonic generally rises exponentially as shown at 115. Second and third harmonic responses typically continue to fall at varying rates as at 120, but there are suggestions that some may be rising again at the upper end of the present excitation range, i.e. above 85 volts.

These general characteristics of the responses are consistent with solvent/solute systems which have not reached a point where major changes in structure have taken place, such as complete removal of a hydration layer or approached cavitation. Energy is being fed into harmonics as excitation increases. The quantitative details of the curves, however, suggest that there is information on which both qualitative and quantitative analysis can be based, as discussed below.

Figure 8:
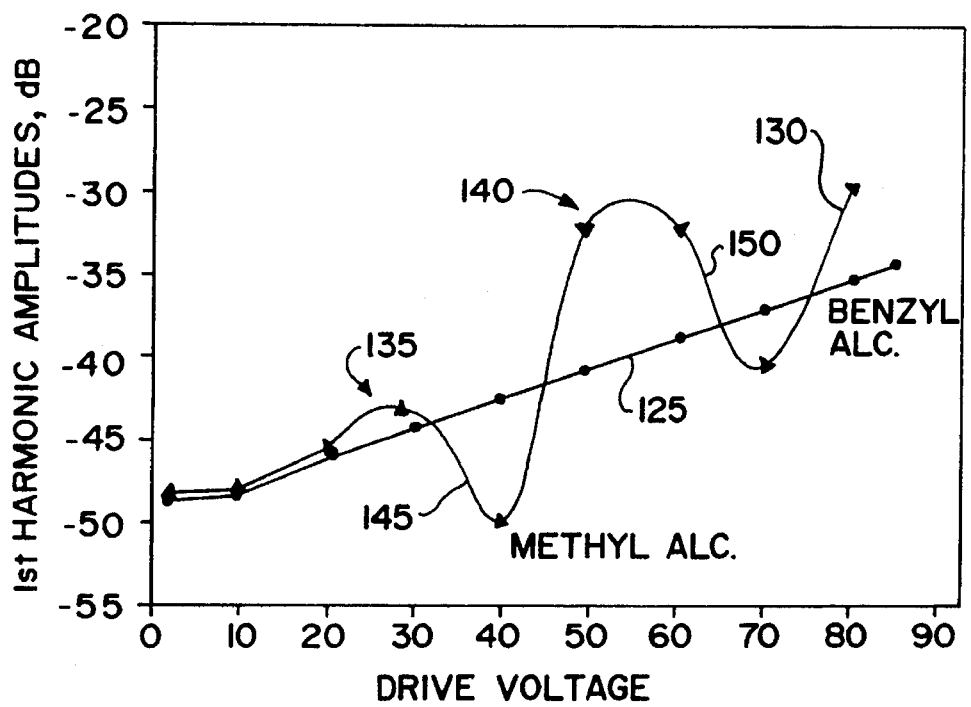
FIG. 8 is a graph of the fundamental amplitude vs. drive voltage for benzyl and methyl alcohols.

FIG. 8 is a comparison plot of the first harmonics for benzyl alcohol, which follow the general exponentially-rising pattern as at 125, and methyl alcohol, which does not, as shown at 130. The two "humps", at 135 and 140, in the exponential response for methyl alcohol occur at inflection points 100 and 105 in the curve of the fundamental (FIG. 6). The nonlinearity actually declines with increasing acoustic intensity during these events before rising again at higher intensities. That the effect happens twice as a function of acoustic intensity in the measurement range suggests that the phenomenon is not simply cavitation, which would be indicated by a single hump. This behavior is consistent with a system in which acoustic intensity during the tensile half-cycle causes a significant structural re-arrangement of the local ordering in methyl alcohol at two different acoustic intensities in this measurement range.

Structural re-arrangement is consistent with, and supports, the working hypothesis that the tensile half-cycle of the sound wave is removing hydration layers and/or portions of layers of the "hydration sphere," in this case the local association of methyl alcohol molecules. Thermodynamically, the free energy supporting the structural rearrangement is supplied from the fundamental response and from the first harmonic over a portion of the range.

That the strength of the nonlinear interaction declines with increasing acoustic intensity in a portion of this process between 30 and 40 Volts as at 145 and between 55 and 70 Volts as at 150 in the FIG. 8, rather than simply saturating, is thought to be related to the same process that causes the initial decline (between 3 and 10 volts) noted in FIG. 7.

It is likely that the lines of FIG. 8 at 145 and 150 are a transitional process reflecting the breakdown of the presently outer, most weakly bound hydration layer. The process seems to involve a relaxation-time process, or the equivalent, to prevent re-association during the compressive half-cycle, and a "hard" shell of well-defined binding energy.

The process can be described in the following terms. The layer or shell is breached, and begins to disintegrate under increasing acoustic intensity. Less tightly bound solvent molecules are dissociated from the layer. Differences in effective inertial mass of the hydrated solute-molecule entities between tensile and compressive half-cycle of the sound wave become less. The generation of harmonics is therefore reduced until increasing acoustic intensity returns the system to an increasingly nonlinear mode through increasing distortion of the remaining portions of the hydration spheres.

It can be postulated that the width of the "hump" or dip is a measure of the cohesion within a hydration layer, and its position a measure of the binding energy. If so, these parameters would be properties of the chemical solution and diagnostic of it. The associated relaxation time(s) would make the process ultrasonic frequency-dependent, which could contribute to the analytical processes.

Figure 9:
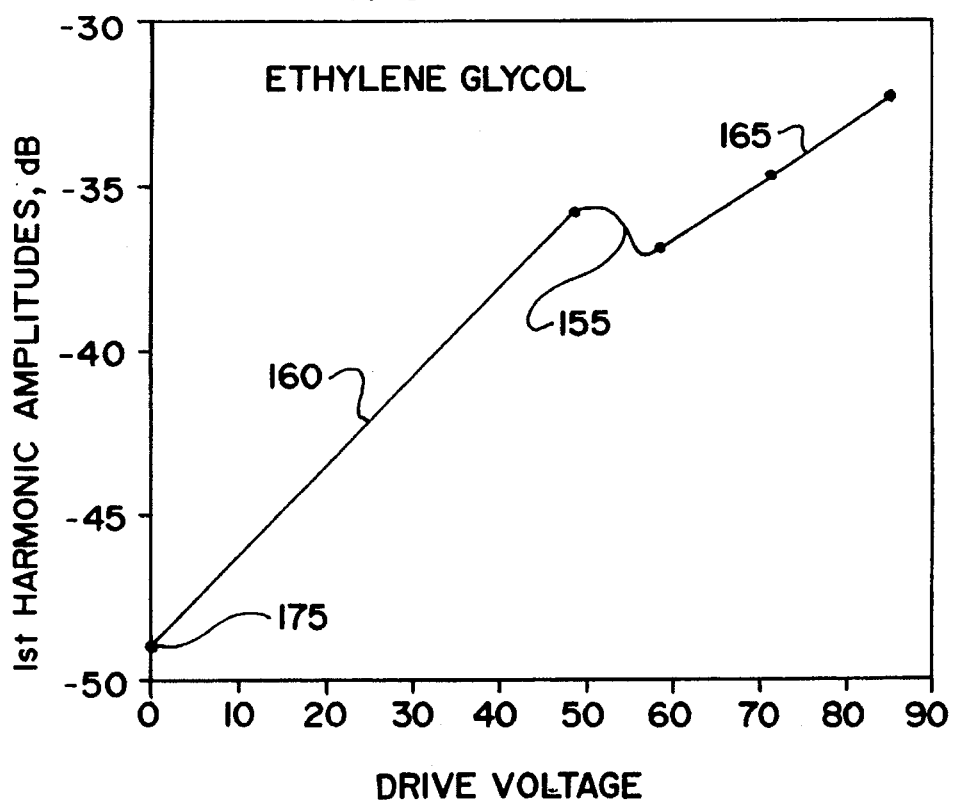
FIG. 9 is a graph of the first harmonic amplitude vs. drive voltage for ethylene glycol.

Similar, though less radical, behavior is exhibited in the results for ethylene glycol, as shown in FIG. 9. In this case there is a break in the first harmonic curve between 50 and 60 V excitation as at 155. The two straight-line segments 160 and 165 are least-square fits which have different slopes. The upper segment 165 has a lower slope (is less nonlinear), consistent with a reduced effective-mass difference on alternate half-cycles, as if a shell had been breached.

Methyl alcohol and ethylene glycol may have reached "saturation" of one or more hydration layers (in terms of the model) within the presently-available acoustic pressure range (as shown in FIGS. 8 and 9). The other materials are expected to exhibit similar discontinuities at higher acoustic intensities.

There are quantitative observations which show that one should also be able to distinguish among solutions qualitatively and to determine solution concentrations quantitatively by analyzing nonlinear effects at lower intensities. Experimental data has been developed for various solutions and also for pure solvents including ethylene glycol, benzyl alcohol, sodium chloride, cesium iodide and pure water. The data has been used to determine an exponential coefficient ($\alpha$) used in the equation for the first harmonic graphs as follows: $R = Ao^{\alpha I}$ where Response R is proportional to Ao, the amplitude at zero intensity as at 170 of FIG. 7 and 175 of FIG. 9, and exponents $\alpha$ and I, the intensity of the sound field. The value of $\alpha$ determines the slope of the lower portion of each curve.

It is observed in FIG. 9 that the amplitude of the first harmonic rises exponentially until saturation or layer-removal begins. The exponential constants differ for each solution in relatively small, but statistically significant amounts as seen in Table 3.

TABLE 3

| Exponential Constants for First Harmonics | |
| --- | --- |
| Solution | Exponential Constant ($\alpha$) |
| Ethylene Glycol | 0.2253 ± 0.0056 |
| Benzyl Alcohol | 0.1735 ± 0.0042 |
| Sodium Chloride | 0.2124 ± 0.0036 |
| Cesium Iodide | 0.1888 ± 0.0012 |
| Water | 0.1941 ± 0.0088 |

The exponential constants were determined by least-square fits to the (logarithmic) amplitude values, excluding the initially-declining points, i.e. values between 3 V and 10 V on FIG. 7. The differences between all pairs of exponential constants in Table 3 are statistically significant ($\chi^2$ test, p <0.05). Ethylene glycol is represented in Table 3 by the first segment 160 in FIG. 9 of its first harmonic.

Within any one solvent/solute system, e.g., different concentrations of dissociated analytes, such as CsI or NaCl, the exponential constants (α) are statistically the same, but the amplitudes (Ao) differ as seen in Table 4.

TABLE 4

| Concentration Dependence | | |
| --- | --- | --- |
| Analyte and Concentration | Amplitude (Ao) | Exponential Constant (α) |
| NaCl, 0.5 M | −48.781 ± 0.191 | 0.2124 ± 0.0036 |
| NaCl (0.1 M and 0.05 M) | −49.543 ± 0.251 | 0.2037 ± 0.0039 |
| Cs I, 0.5 M | −48.793 ± 0.064 | 0.1888 ± 0.0012 |
| CsI + I (0.1 M and 0.05 M) | −48.280 ± 0.138 | 0.1890 ± 0.0062 |

Reviewing the data in Table 4 for NaCl solutions, it should be noted the graph of FIG. 7 has an Ao intercept of about 48.7 dB, equivalent to a 0.5M solution of Table 4. The graph for the less concentrated solutions, i.e. 0.01 and 0.05M would run parallel to the line 115 but about 0.8 dB below line 115. The slope for each would be the same since the values of exponential constant (α) for each analyte are statistically the same ($\chi^2$ test, p>0.05) for the two concentrations within each analyte; however, the Ao amplitudes differ significantly ($\chi^2$ test, p<0.05).

The values of the exponential constant α may be used to determine the identity of at least a single-solute system as well as solute concentration, even when the intensity has not been sufficient to cause saturation or related effects.

These results can be understood in terms of the model on the basis that the molecular interactions which determine the exponential constant α are unique to the hydration of each solvent/solute component, while the harmonic amplitude Ao is a measure of the number of such interactions per unit volume, i.e. the concentration. These survey measurements have shown that methyl alcohol and ethylene glycol can be distinguished from each other and from the other solutions tested simply by the shape of their curves of the first harmonic amplitude vs. acoustic pressure which is proportional to the transducer drive voltage. Methyl alcohol is the most volatile of the experimental materials and therefore the one expected to have the least local binding energy for hydration-like effects. Both materials behave in a manner that supports the key features of the hydration model for the physics of nonlinear acoustic propagation in solvents.

This hydration model predicts that each of the other materials will show similar behavior at the appropriate acoustic intensity; that the appropriate intensity will occur before the solution cavitates; and that the shapes of the curves will be essentially unique to the particular solvent/solute system.

It is also shown that the curves describing the growth of harmonic content with increasing acoustic intensity provide information that can be used to define the solvent/solute system and the concentration of the solute, even at acoustic pressures below those necessary to cause the kinds of effects observed in methyl alcohol and ethylene glycol. These quantitative effects, by themselves, appear to be sufficient to provide the basis for a quantitative and qualitative chemical analysis system which can do the analysis from outside a sealed container.

In terms of the model, the two types of observations are different aspects of the same phenomenon. The difference between them is simply a matter of acoustic intensity. The strength of the nonlinearity as measured by the first harmonic at any acoustic intensity depends on the details of molecular interactions between solvent and solute. The intensity dependence is exponential until one or more threshold intensities are reached; the amplitude of the exponential term depends on the number of solvent/solute interactions per unit volume, while the exponential constant measures the strength of the interactions. At intensities significantly above each threshold the nonlinear strength increases exponentially again, but at a lesser rate, indicating a smaller effective mass difference between alternate halves of the sound cycle. The mass difference is lower because a hydration layer has been removed. The intensity thresholds are interpreted here as a measure of the binding energy of "hard" hydration layers or shells, which are quantitatively unique properties of each solvent/solute system. It is expected that saturation-like effects, the humps and dips or breaks, from more than one solute will be superimposed on the curve allowing each solute to be identified, and that the amplitudes of these humps will be related to concentration.

Figure 10:
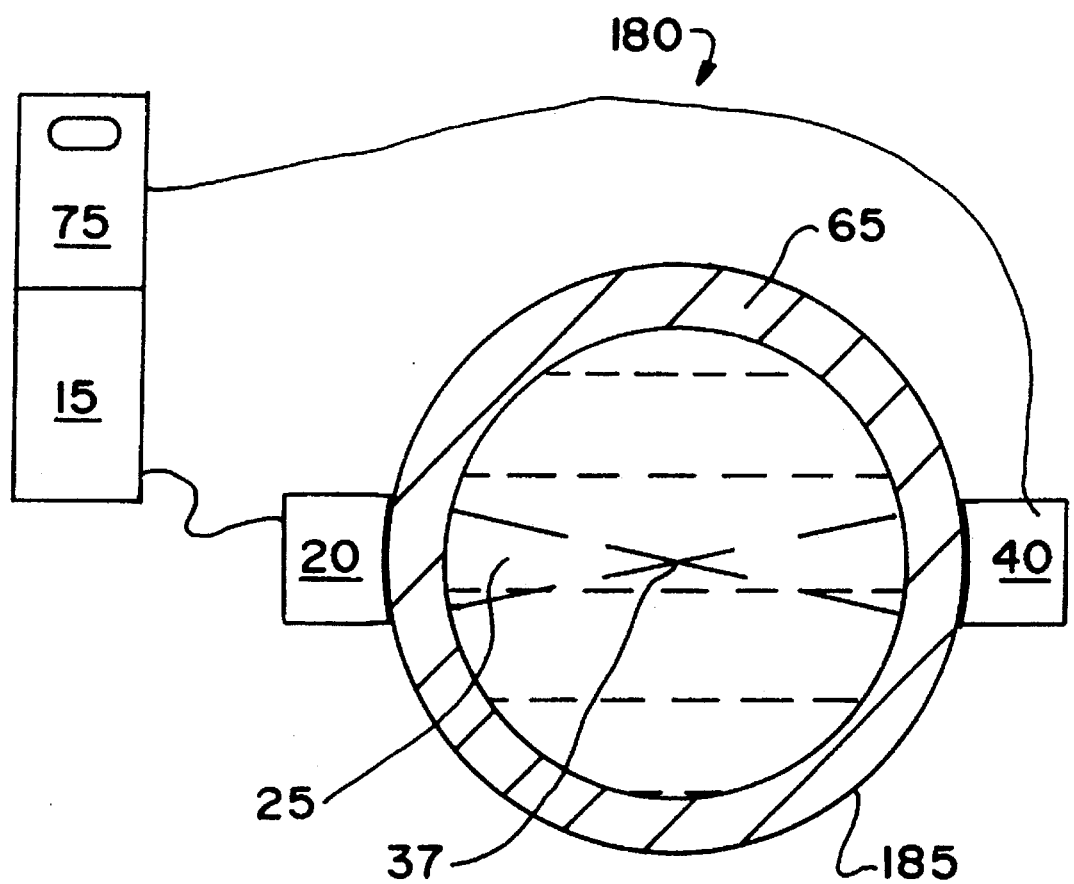
FIG. 10 is a schematic diagram of a preferred embodiment of the acoustic apparatus.

In a preferred embodiment, FIG. 10 discloses an apparatus 180 for directly measuring the type and concentration of a solution within a container, vessel or pipe 180, shown in cross section, and, having input electronics 15, acoustic transducer 20, field probe 40, and output electronics 75. In this case, the acoustic beam 25 is focused within the pipe 185 at focal point 37 and the method used is similar to the experimental apparatus of FIG. 4 without the container 45 and water bath. The field probe 40 is placed against the vessel 185 on an opposing side from the transducer 20 to obtain a maximum acoustic signal. The apparatus is portable and can be hand held for easy solution testing.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

What is claimed is:

1. A method of analyzing a solution by acoustic means, the method comprising:

immersing a sound focusing transducer within a first liquid filled container;

locating a specimen solution contained within a second container at a sound focal point within the first container;

locating a sound probe adjacent to the specimen;

generating a variable intensity sound signal from the transducer;

measuring a fundamental and multiple harmonic sound signal amplitudes; and then comparing a plot of a sound response of the specimen with a known solution sound response, thereby determining the solution type and concentration of the specimen.

2. The method of claim 1 wherein a semilogarithmic plot of specimen amplitude of a first harmonic vs. sound intensity is used to determine a value of an exponential constant and a zero intensity amplitude thereby identifying a solution and its concentration.

3. The method of claim 2 wherein the plot of amplitude vs. sound intensity follows the equation: $R = Ao^{\alpha I}$ where: R is sound amplitude, Ao is zero intensity amplitude, α is an exponential constant, and I is sound intensity.

4. The method of claim 3 wherein the variable intensity sound signal is increased to a value wherein a change in the exponential value of α qualitatively identifies a chemical solution.

5. The method of claim 2 wherein the exponential constant qualitatively determines a solution and a zero intensity amplitude determines a solution concentration.

6. The method of claim 1 wherein the variable intensity sound signal is at least one MHz creating a peak acoustic pressure of less than a cavitation intensity for the solution.

7. The method of claim 1 wherein the variable intensity sound signal is less than a specimen cavitation intensity and equal to or greater than an intensity that creates a specimen hydration layer partial or complete removal.

8. An acoustic apparatus for quantitatively and qualitatively analyzing a solution comprising:
   a) input electronics that generate a variable intensity acoustic signal;
   b) a beaming acoustic transducer within a fluid bath;
   c) a container holding an unknown specimen solution located at an acoustic focal point within the fluid bath;
   d) an ultrasonic field probe placed in the fluid bath far field beyond the focal point;
   e) output electronics that monitor and indicate the amplitude of a fundamental and a harmonic acoustic signal from the field probe, as a function of the variable intensity acoustic signal.

9. The apparatus of claim 8 wherein the beaming acoustic transducer has means to transmit a signal intensity in the range of less than a cavitation intensity at the focal point to a value that causes a change in slope in a semilogarithmic plot of specimen harmonic amplitude vs. Sound intensity, thereby determining a type and concentration of the specimen solution.

10. A method of analyzing an unknown solution within a vessel by acoustic means, the method comprising:

placing a sound focusing transducer in contact with the vessel containing the unknown solution;

locating a sound probe in contact with the vessel;

generating a variable intensity sound signal from the transducer;

measuring a fundamental and multiple harmonic sound signal amplitudes; and then comparing a plot of a sound response of the specimen with a known solution sound response, thereby determining the solution type and concentration of the specimen.

11. The method of claim 10 wherein a semilogarithmic plot of specimen amplitude of a first harmonic vs. sound intensity is used to determine a value of an exponential constant and a zero intensity amplitude thereby identifying a solution and its concentration.

12. The method of claim 11 wherein the plot of amplitude vs. sound intensity follows the equation: $R = A_o e^{\alpha I}$ where: R is sound amplitude, Ao is zero intensity amplitude, $\alpha$ is an exponential constant, and I is sound intensity.

13. The method of claim 12 wherein the variable intensity sound signal is increased to a value wherein a change in the exponential value of $\alpha$ qualitatively identifies a chemical solution.

14. The method of claim 11 wherein the exponential constant qualitatively determines a solution and a zero intensity amplitude determines a solution concentration.

15. The method of claim 10 wherein the variable intensity sound signal is at least one MHz creating a peak acoustic pressure of less than a cavitation intensity for the solution.

16. The method of claim 10 wherein the variable intensity sound signal is less than a specimen cavitation intensity and equal to or greater than an intensity that creates a specimen hydration layer partial or complete removal.

* * * * *